US007186853B2

(12) United States Patent
Enlow et al.

(10) Patent No.: US 7,186,853 B2
(45) Date of Patent: Mar. 6, 2007

(54) POLYMER COMPOSITIONS CONTAINING STABILIZER COMPOUNDS COMPRISING TRICYCLODECYLMETHYL GROUPS

(75) Inventors: William Palmer Enlow, Belpre, OH (US); Marshall D. Moore, Morgantown, WV (US); Vaikunth Sitaram Prabhu, Morgantown, WV (US); Tilak T. Raj, Bangalore (IN); Arakali S. Radhakrishna, Bangalore (IN); Timmanna Upadhya, Bangalore (IN); Surendra U. Kulkarni, Bangalore (IN)

(73) Assignee: Crompton Corporation, Middlebury, CT (US)

( * ) Notice: Subject to any disclaimer, the term of this patent is extended or adjusted under 35 U.S.C. 154(b) by 0 days.

(21) Appl. No.: 10/455,027

(22) Filed: Jun. 5, 2003

(65) Prior Publication Data

US 2004/0249030 A1 Dec. 9, 2004

(51) Int. Cl.
*C07F 9/02* (2006.01)
(52) U.S. Cl. .................. 558/218; 514/75; 514/506; 524/115
(58) Field of Classification Search ............... 558/218; 514/75, 506; 524/115
See application file for complete search history.

(56) References Cited

U.S. PATENT DOCUMENTS

| 3,751,528 | A | | 8/1973 | Inamoto et al. ............... 45/54 |
| 4,078,022 | A | * | 3/1978 | Chen ........................ 558/209 |
| 4,082,723 | A | * | 4/1978 | Mayer et al. ................ 524/83 |
| 4,443,572 | A | | 4/1984 | Burns ........................ 524/120 |
| 5,844,029 | A | | 12/1998 | Prabhu et al. ............. 524/236 |
| 5,880,191 | A | | 3/1999 | Prabhu et al. ............. 524/236 |
| 5,922,794 | A | | 7/1999 | Prabbhu et al. ............. 524/236 |
| 5,969,015 | A | | 10/1999 | Zinke et al. ................ 524/109 |
| 6,103,798 | A | | 8/2000 | Prabhu et al. ............. 524/236 |
| 6,362,260 | B1 | | 3/2002 | Stevenson et al. ......... 524/115 |

FOREIGN PATENT DOCUMENTS

| EP | 0930332 A2 | 7/1999 |
| GB | 1532709 | 11/1978 |
| GB | 1561414 | 2/1980 |

\* cited by examiner

*Primary Examiner*—Peter D. Mulcahy
(74) *Attorney, Agent, or Firm*—Daniel Reitenbach

(57) ABSTRACT

The invention relates to phosphites comprising substituted or unsubstituted tricyclodecylmethyl groups. The phosphites may also contain substituted and unsubstituted alcohols having about C6–C18 carbon atoms. The alcohol chain may be aliphatic, arylakyl and alkylaryl groups. The method of making of the phosphite composition is also described.

6 Claims, No Drawings

POLYMER COMPOSITIONS CONTAINING STABILIZER COMPOUNDS COMPRISING TRICYCLODECYLMETHYL GROUPS

FIELD OF THE INVENTION

The invention relates generally to compositions and stabilizers for polymer resin compositions, and more particularly relates to stabilized resin compositions and stabilizer concentrates for polymer resin compositions.

BACKGROUND OF THE INVENTION

Stabilization is defined as protection of deterioration of the polymeric compositions during processing at high temperatures. This is needed in a number of applications to enhance resistance to thermal and light degradation and withstand more rigorous conditions. Stabilization in polymer compositions is typically achieved by incorporation of certain additive compounds. Broadly, these additives could be classified as phenolics (for example hindered phenolics) and non-phenolics (for example hydroxylamines, amine oxides, lactones, thioesters and phosphites). The non-phenolic stabilizers are disclosed in U.S. Pat. Nos. 4,403,053; 4,305,866 and 5,922,794, which discloses stabilization of polyolefins with a benzotriazole and a phosphite, a phosphite, and stabilization of polymers with tertiary amine oxide, based stabilizers respectively. U.S. Pat. No. 5,969,015 discloses monomeric or oligomeric bisphosphites as stabilizers for poly (vinyl chloride). The use of alkyl pentaerythritol phosphite as a thermal stabilizer for vinyl polymers has been disclosed in U.S. Pat. No. 6,362,260. U.S. Pat. No. 4,443,572 discloses stabilization of polyolefins with phosphites, hindered phenols and thioesters. These stabilizers do have some drawbacks. Stabilized polymer compositions containing certain phenolic antioxidants and hindered amine stabilizers tend to discolor upon storage. In addition these stabilizer could decompose and volatilize at high temperature and condensation of these volatile components as "fog" on the surface of the polymer composition. This is more prevalent with the presence of phenols.

Typically, phosphites are a class of secondary anti-oxidants and are often prone to hydrolysis. It is therefore important to have a high hydrolytic resistance. Good stabilizer should have a high thermal stability coupled with low volatility and high hydrolytic resistance. A preferred phosphite for use with mixed metal stabilizers is diphenyl isodecyl phosphite, but this generates phenol upon hydrolysis. Another stabilizer tris-(nonylphenyl) phosphite (hereinafter sometimes referred to by the abbreviation, "TNPP") used along with tri-isopropanolamine to improve the hydrolytic stability for polyolefins.

There is a drive in polymer industry to have a non-phenol based material meeting the performance requirement of TNPP in polymers. There is also a need to develop alternate stabilizer that over come certain issues that phenolic stabilizers have as mentioned above. The known stabilizers do not satisfy all requirements with regard to factors, such as, shelf-life, water absorption, sensitivity to hydrolysis, and in-process stabilization. As a result, there continues to be a need for effective stabilizers for organic polymers. There is also a need to eliminate or minimize phenol content in the phosphite stabilizers and still have a stabilizer, which gives good color, hydrolytic and processing stability. Furthermore, it may be important to have a "green" or non-phenolic requirement while meeting the performance and cost criteria of the stabilizer and replace phenyl or substituted phenyl esters on a long term basis in the years to come.

SUMMARY OF THE INVENTION

The invention relates to phosphites comprising substituted or unsubstituted tricyclodecylmethyl groups. The phosphites may also contain substituted and unsubstituted alcohols having about C6–C18 carbon atoms. They may be aliphatic, arylakyl and alkylaryl groups.

The invention further relates to a method for preparing phosphites comprising tricyclodecylmethyl groups.

Yet another embodiment of the present invention relates to a stabilized polymer resin composition comprising a polymer resin, and phosphites comprising tricyclodecylmethyl groups.

Still another embodiment of the present invention relates to a method for making a stabilized polymer resin composition. The method comprises mixing a phosphite comprising tricyclodecylmethyl groups with a polymer resin.

DETAILED DESCRIPTION OF THE INVENTION

As used herein, the term "stabilizing" means improving the stability of a polymer composition during extrusion or polymer processing, or against exposure to severe conditions, and the like. Further, the term "stabilization" may also mean improving the stability of the polymer against changes in molecular weight, melt flow index, color degradation, e.g. in the yellowness index of the polymer during extrusion or similar polymer processing operations. In another embodiment, stabilization may mean to improve the stability of the polymer due to degradation upon exposure to weathering, heat, light, and/or the elements. The words polymer and polymer resin are used interchangeably and refer to the same unless the context clearly dictates otherwise.

As used herein, a "stabilizing amount" is meant an amount effective to improve the polymer resin stabilization against, for example, molecular weight degradation, color degradation, or molecular weight degradation and color degradation from melt processing, from weathering, and/or from long term field exposure to heat, light, and/or the elements.

The present invention relates to a composition comprising a polymer resin, and an effective stabilizing amount of a new class of stabilizing additives comprising substituted and unsubstituted tricyclodecylmethyl phosphites. In one embodiment, the tricyclodecylmethyl phosphites stabilizers of the present invention have also been found to work synergistically with other stabilizers known in the prior art. Polymer resin compositions comprising the tricyclodecylmethyl phosphites show excellent hydrolytic stability.

POLYMER RESIN COMPONENT: The polymer resin component may be any thermoplastic polymer resin or thermoset polymer resin known in the art. Non-limiting examples of thermoplastic polymers include polyolefin homopolymers and copolymers, polyesters, polyurethanes, polyalkylene terephthalates, polysulfones, polyimides, polyphenylene ethers, styrenic polymers and copolymers, polycarbonates, acrylic polymers, polyamides, polyacetals, and halide containing polymers, and blends thereof. Mixtures of different polymers, such as polyphenylene ether-styrenic resin blends, polyvinyl chloride-Acrylonitrile-buta diene-styrene (also sometimes hereinafter called "ABS") or other impact modified polymers, such as methacrylonitrile and alpha-methylstyrene containing ABS, and polyester-ABS or polycarbonate-ABS and polyester plus some other impact modifier may also be used. Such polymers are available commercially or may be made by means well known in the art.

The tricyclodecylmethyl phosphite compounds may also be useful in stabilizing thermoset resin compositions, such as polyurethanes, epoxides, melamine, and phenolics; and may be useful in thermoset plastic blends.

Polymer resins of monoolefins and diolefins include, for example polypropylene, polyisobutylene, polybutene-1, polymethylpentene-1, polyisoprene, or polybutadiene, as well as polymers of cycloolefins, for instance of cyclopentene or norbornene, polyethylene (which optionally can be crosslinked), for example high density polyethylene (HDPE), low density polyethylene (LDPE), very low density polyethylene (VLDPE) and linear low density polyethylene (LLDPE) may be used. Mixtures of these polymers, for example, mixtures of polypropylene with polyisobutylene, polypropylene with polyethylene (for example PP-HDPE, PP-LDPE) and mixtures of different types of polyethylene (for example LDPE-HDPE), may also be used. Also useful are copolymers of monoolefins and diolefins with each other or with other vinyl monomers, such as, for example, ethylene-propylene, LLDPE and its mixtures with LDPE, propylene-butene-1, ethylene-hexene, ethylene-ethylpentene, ethylene-heptene, ethylene-octene, propylene-isobutylene, ethylene-butene-1, propylene-butadiene, isobutylene, isoprene, ethylene-alkyl acrylates, ethylene-alkyl methacrylates, ethylene-vinyl acetate (EVA) or ethylene-acrylic acid copolymers (EAA) and their salts (ionomers) and terpolymers of ethylene with propylene and a diene, such as hexadiene, dicyclopentadiene or ethylidene-norbornene; as well as mixtures of such copolymers and their mixtures with polymers resins mentioned above, for example polypropylene-ethylene propylene-copolymers, LDPE-EVA, LDPE-EAA, LLDPE-EVA, and LLDPE-EAA.

The polymers resins of the present invention may also include styrenic polymers, such as polystyrene, poly-(p-methylstyrene), poly-(.alpha.-methylstyrene), copolymers of styrene or .alpha.-methylstyrene with dienes or acrylic derivatives, such as, for example, styrene/butadiene, styrene/acrylonitrile, styrene/alkyl methacrylate, styrene/maleic anhydride, styrene/maleimide, styrene/butadiene/ethyl acrylate, styrene/acrylonitrile/methyl acrylate, mixtures of high impact strength from styrene copolymers and another polymer, such as, for example, from a polyacrylate, a diene polymer or an ethylene/propylene/diene terpolymer; and block copolymers of styrene, such as, for example, styrene/butadiene/styrene, styrene/isoprene/styrene, styrene/ethylene/butylene/styrene or styrene/ethylene/propylene styrene. Styrenic polymers may additionally or alternatively include graft copolymers of styrene or alpha.-methylstyrene, such as for example, styrene on polybutadiene, styrene on polybutadiene-styrene or polybutadiene-acrylonitrile; styrene and acrylonitrile (or methacrylonitrile) on polybutadiene and copolymers thereof; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene-propylene-diene terpolymers, styrene and acrylonitrile on polyacrylates or polymethacrylates, styrene and acrylonitrile on acrylate/butadiene copolymers, as well as mixtures thereof with the styrenic copolymers indicated above.

Nitrile polymers are also useful in the polymer composition of the invention. These include homopolymers and copolymers of acrylonitrile and its analogs, such as polymethacrylonitrile, polyacrylonitrile, acrylonitrile/butadiene polymers, acrylonitrile/alkyl acrylate polymers, acrylonitrile/alkyl methacrylate/butadiene polymers, and various ABS compositions as referred to above in regard to styrenics.

Polymer resins based on acrylic acids, such as acrylic acid, methacrylic acid, methyl methacrylic acid and ethacrylic acid and esters thereof may also be used. Such polymers include polymethylmethacrylate, and ABS-type graft copolymers wherein all or part of the acrylonitrile-type monomer has been replaced by an acrylic acid ester or an acrylic acid amide. Polymers including other acrylic-type monomers, such as acrolein, methacrolein, acrylamide, and methacrylamide may also be used.

Halogen-containing polymers that may be used include resins, such as polychloroprene, epichlorohydrin homopolymers- and copolymers, polyvinyl chloride, polyvinyl bromide, polyvinyl fluoride, polyvinylidene chloride, chlorinated polyethylene, chlorinated polypropylene, fluorinated polyvinylidene, brominated polyethylene, chlorinated rubber, vinyl chloride-vinyl acetate copolymers, vinyl chloride-ethylene copolymer, vinyl chloride-propylene copolymer, vinyl chloride-styrene copolymer, vinyl chloride-isobutylene copolymer, vinyl chloride-vinylidene chloride copolymer, vinyl chloride-styrene-maleic anhydride terpolymer, vinyl chloride-styrene-acrylonitrile copolymer, vinyl chloride-butadiene copolymer, vinyl chloride-isoprene copolymer, vinyl chloride-chlorinated propylene copolymer, vinyl chloride-vinylidene chloride-vinyl acetate terpolymer, vinyl chloride-acrylic acid ester copolymers, vinyl chloride-maleic acid ester copolymers, vinyl chloride-methacrylic acid ester copolymers, vinyl chloride-acrylonitrile copolymer and internally plasticized polyvinyl chloride.

Other useful polymer resins include homopolymers and copolymers of cyclic ethers, such as polyalkylene glycols, polyethylene oxide, polypropylene oxide or copolymers thereof with bis-glycidyl ethers; polyacetals, such as polyoxymethylene and those polyoxymethylenes which contain ethylene oxide as a comonomer; polyacetals modified with thermoplastic polyurethanes, acrylates or methacrylonitrile containing ABS; polyphenylene oxides and sulfides, and mixtures of polyphenylene oxides with polystyrene or polyamides; polycarbonates and polyestercarbonates; polysulfones, polyethersulfones and polyetherketones; and polyesters which are derived from dicarboxylic acids and diols and/or from hydroxycarboxylic acids or the corresponding lactones, such as polyethylene terephthalate, polybutylene terephthalate, poly-1,4dimethylol-cyclohexane terephthalate, poly-2(2,2,4(4-hydroxyphenyl)-propane) terephthalate, and polyhydroxybenzoates; as well as block copolyetheresters derived from polyethers having hydroxyl end groups.

Suitable polymer resins also include polyamides and copolyamides derived from bisamines and dicarboxylic acids and/or from aminocarboxylic acids or the corresponding lactams, such as polyamide 4, polyamide 6, polyamide 6/6, 6/10, 6/9, 6/12 and 4/6, polyamide 11, polyamide 12, aromatic polyamides obtained by condensation of m-xylene bisamine and adipic acid; polyamides prepared from hexamethylene bisamine and isophthalic and/or/ terephthalic acid and optionally an elastomer as modifier, for example poly-2,4,4 trimethylhexamethylene terephthalamide or poly-m-phenylene isophthalamide. In other embodiments, copolymers of the aforementioned polyamides with polyolefins, olefin copolymers, ionomers, or chemically bonded or grafted elastomers; or with polyethers, such as for instance, with polyethylene glycol, polypropylene glycol or polytetramethylene glycols and polyamides or copolyamides modified with ethylene propylene diene monomer (EPDM) or ABS may be used.

In one embodiment, the thermoplastic polymer is one of polyolefins, polycarbonates, polyesters, polyphenylene ethers and styrenic polymers, or a mixture thereof. In another embodiment, the polymer is one of polyethylene, polypropylene, polyethylene terephthalate, polyphenylene ether homopolymers and copolymers, polystyrene, high impact polystyrene, polycarbonates and ABS-type graft copolymers and mixtures thereof.

In one embodiment, the polymer resin is in a range between about 50 and about 99.99 percent by weight based on the total weight of the composition. In a second embodiment, the resin is in a range between about 80 and about 99.9 percent by weight based on the total weight of the composition. In a third embodiment, the resin is in a range between about 95 and about 99 percent by weight based on the total weight of the composition.

STABILIZER COMPONENT(S). The inventors have discovered that tricyclodecylmethyl phosphite compounds may surprisingly be used as stabilizers for polymer resin compositions, in view of their high hydrolytic stability and activity.

In one embodiment, the phosphite-based stabilizer compound comprises one to three substituted and unsubstituted tricyclodecylmethyl groups. In yet another embodiment of the invention, the phosphite compound is of the general formula:

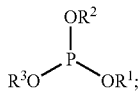

wherein $R^1$ is a substituted or an unsubstituted tricyclodecylmethyl group; and $R^2$ and $R^3$ are independently selected from the group consisting of substituted and unsubstituted tricyclodecylmethyl groups, and substituted and unsubstituted $C_6$–$C_{18}$ aliphatic, alkylaryl and arylalkyl groups.

In another embodiment, the stabilizer compound is a phosphite based compound of the formula

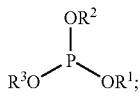

wherein $R^1$ is a 5-tricyclodecylmethyl group, $R^2$ and $R^3$ are independently selected from $C_8$–$C_{18}$ aliphatic, alkylaryl and arylalkyl groups. In another embodiment, $R^2$ and $R^3$ are independently selected from substituted and unsubstituted n-octyl, iso-octyl, tricyclodecyl, n-decyl, iso-decyl, 2-benzylheptyl, dodecyl, tetradecyl, hexadecyl and octadecyl groups. In another embodiment, $R^2$ and $R^3$ are independently selected from n-octyl, iso-octyl, n-decyl, iso-decyl, 2-benzylheptyl, dodecyl, tetradecyl, hexadecyl and octadecyl groups.

In a particular embodiment, the stabilizer compound is a phosphite based compound of the formula:

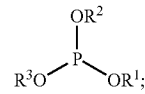

wherein $R^1$, $R^2$, and $R^3$ are 5-tricyclodecylmethyl groups.

The phosphite of the present invention may be synthesized via the trans-esterification route in high yield and purity. The first step in the preparation of the phosphite of the present invention is to heat a mixture of tricyclodecyl methanol with triaryl phosphite and a catalyst. Tricyclodecyl methanol is commercially available from various sources, e.g., Celanese Corporation under trade name TCD-Alcohol M and TCD-Alcohol DM. These are typically obtained from the corresponding oxoformylation of the respective dienes followed by reduction. In one embodiment, the alkali metal salts of lower alcohols with about 1–4 carbon atoms and substituted and unsubstituted phenols are employed as catalyst to aid the reaction. In another embodiment, the catalyst comprise of lithium, sodium or potassium salts of lower alcohols with about 1–4 carbon atoms and substituted and unsubstituted phenols. The catalyst is present in an "effective amount" i.e., an amount effective to help catalyze the reaction.

In one embodiment the triaryl phosphite is triphenyl phosphite, triphenylphosphite, tri-(2,4-di-tert-butylphenyl) phosphite, tetrakis(2,4-di-tert-butylphenyl)-4,4'-biphenylene diphosphonite. In one embodiment of the present invention, the mole ratio of the tricyclodecylmethanol to the triaryl phosphite is in the range of about 3:1 to about 3.5:1. The reaction is heated to about 135° C. for a couple of hours. The above reaction is cooled. The excess of the hydroxy substituted aromatic hydrocarbon (also sometimes hereinafter called "aromatic hydroxy compound") that is generated as a by-product in the above reaction is removed from the above mixture. The removal of the aromatic hydroxy compound could be carried out using various techniques such as distillation under reduced pressure or thermally. The distillation of the aromatic hydroxy compound drives the reaction in the forward direction to give a reaction mixture defined as the first reaction mixture. In one embodiment of the present invention the aromatic hydroxy compound is removed under reduced pressure of about 30 millimeters of mercury.

In one embodiment, the next step in the synthesis of the phosphite is to add a reactive alcohol to the first reaction mixture. The above reactive mixture is defined as the second reaction mixture. The reactive alcohol is a primary or secondary alcohol. The reactive alcohol may be substituted and unsubstituted tricyclodecylmethanols, substituted and unsubstituted aliphatic and aromatic alcohols with the number of carbon atoms are in the range of about 1 to about 18. In another embodiment, the reactive alcohol is a primary or secondary alcohols either aliphatic, arylalkyl and alkylaryl groups containing about 6 to about 18 carbon atoms. The reactive alcohol may also have a heteroatom present in the chain like —O—, —S—, —SO—, COO—, —CO, —CON— functionalities. The second reaction mixture is heated to about 135° C. The aromatic alcohol by-product and any unreacted alcohol. The reaction is cooled and the colorless phosphite of the present invention is obtained in high yield of about 98 percent.

In one embodiment, the stabilizing additive compound and any reaction products thereof are present in an "effective stabilizing amount" or a "stabilizing amount," i.e., an amount effective to improve the stability of the resin composition. In another embodiment, the amount of the phosphite stabilizer compound is generally less than about 5 weight percent based on the weight of the resin. In a third embodiment, the phosphite compound is present in an amount less than about 5000 parts by weight per million based on the weight of the resin; and in a fourth embodiment, from about 500 parts by weight per million and about 2000 parts by weight per million based on the weight of the resin.

OPTIONAL STABILIZER COMPONENTS. In one embodiment, stabilizers of the prior art, such as for example, hindered phenols, hindered amines, and mixtures thereof, may be optionally added to work in combination with and augment the stabilizers of the present invention.

In one embodiment, the optional stabilizer or mixture of second stabilizers is selected from the group consisting of the phenolic antioxidants, hindered amine stabilizers, the ultraviolet light absorbers, organo-phosphorous compounds comprising of organo-phosphites and organo-phosphonites, alkaline metal salts of fatty acids, the hydrotalcites, metal oxides, epoxydized soybean oils, the hydroxyl amines, the tertiary amine oxides, thermal reaction products of tertiary amine oxides, and the thiosynergists, as further described below. In one embodiment, the organo phosphites are non tricyclodecylmethyl containing phosphites of the present invention that have been described above.

The second stabilizer additive may be an antioxidant selected from alkylated mono-phenols, such as, 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(.alpha.-methylcyclohexyl)-4,6-dimethylphenol, 2,6-di-octadecyl-4-methylphenol, 2,4,6,-tricyclohexyphenol, 2,6-di-tert-butyl-4-methoxymethylphenol, and the like; alkylated hydroquinones, such as for example, 2,6-di-tert-butyl-4-methoxyphenol, 2,5-di-tert-butylhydroquinone, 2,5-di-tert-amyl-hydroquinone, 2,6-diphenyl-4-octadecyloxyphenol, and the like. Suitable antioxidants may also comprise hydroxylated thiodiphenyl ethers, non-limiting examples of which include 2,2'-thio-bis-(6-tert-butyl-4-methylphenol), 2,2'-thio-bis-(4-octylphenol), 4,4'-thio-bis-(6-tertbutyl-3-methylphenol), and 4,4'-thio-bis-(6-tert-butyl-2-methylphenol).

Alkylidene-bisphenols may be used as antioxidants as for example, 2,2'-methylene-bis-(6-tert-butyl-4-methylphenol), 2,2'-methylene-bis-(6-tert-butyl-4-ethylphenol), 2,2'-methylene-bis-(4-methyl-6-(.alpha.-methylcyclohexyl)phenol), 2,2'-methylene-bis-(4-methyl-6-cyclohexylphenol), 2,2'-methylene-bis-(6-nonyl-4-methylphenol), 2,2'-methylene-bis-(6-nonyl-4-methylphenol), 2,2'-methylene-bis-(6(.alpha.-methylbenzyl)-4-nonylphenol), 2,2'-methylene-bis-(6-(.alpha.,.alpha.-dimethylbenzyl)-4-nonyl-phenol).2,2'-methylene-bis-(4,6-di-tert-butylphenol), 2,2'-ethylidene-bis-(6-tert-butyl-4-isobutylphenol), 4,4'-methylene-bis-(2,6-di-tert-butylphenol), 4,4'-methylene-bis-(6-tert-butyl-2-methylphenol), 1,1-bis-(5-tert-butyl-4-hydroxy-2-methylphenol)butane 2,6-di-(3-tert-butyl-5-methyl-2-hydroxybenzyl)-4-methylphenol, 1,1,3-tris-(5-tert-butyl-4-hydroxy-2-methylphenyl)butane, 1,1-bis-(5-tert-butyl-4-hydroxy-2-methylphenyl)-3-dodecyl-mercaptobutane, ethyleneglycol-bis-(3,3,-bis-(3'-tert-butyl-4'-hydroxyphenyl)-butyrate)-di-(3-tert-butyl-4-hydroxy-5-methylpenyl)-dicyclopentadiene, di-(2-(3'-tert-butyl-2'hydroxy-5'methylbenzyl)-6-tert-butyl-4-methylphenyl)terephthalate, and other phenolics such as monoacrylate esters of bisphenols such as ethylidiene bis-2,4-di-tertbutylphenol monoacrylate ester and esters of 3,5-di-butyl hydroxyphenyl propionic acid.

In one embodiment, the second stabilizer is a phenolic antioxidant selected from the group consisting of n-octadecyl, 3,5-di-tert-butyl-4-hydroxyhydrocinnamate, neopentanetetrayl, tetrakis(3,5-di-tert-butyl-4-hydroxyhydrocinnamate), tetrakis [methylene(3,5-di-tert-butyl-4-hydroxyhydrocinnamate)methane], di-n-octadecyl-3,5-di-tert-butyl4-hydroxybenzylphosphonate, 1,3,5-tris(3,5-di-tert-butyl-4-hydroxybenzyl)-isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl)benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4-tert-butyl-3-hydroxybenzyl)isocyanurate, 1,1,3-tris(2-methyl-4-hydroxy-5-tert-butylphenyl)butane, 1,3,5-tris[2-(3,5-di-tert-butyl-4-hydroxyhydrocinnamoyloxy)ethyl] isocyanurate, 3,5-di-(3,5-di-tert-butyl-4-hydroxybenzyl) mesitol, hexamethylene bis(3,5-di-tert-butyl-4-hyroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl-3,5-di-tert-butyl-4-hydroxybenzylphosphonate), ethylene bis [3,3-di(3-tert-butyl-4-hydroxyphenyl)butyrate], octyl-3,5-di-tert-butyl-4-hydroxybenzylmercaptoacetate, bis(3,5-di-tert-butyl-4-hydroxyhydrocinnamoyl)hydrazide, and N,N'-bis-[2-(3,5-di-tert-butyl-4-hydroxyhydrocinnamoyloxy)ethyl]-oxamide.

In another embodiment the phenolic antioxidant is selected from a group consisting of octadecyl-3,5-di-tert-butyl-4-hydroxycinnamate, tetrakis[methylene(3,5-di-tert-butyl-4-hydroxyhydrocinnamate)]methane, 1,3,5-tris(3,5-di-tert-butyl-4-hydroxybenzyl)isocyanurate, tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl4-hydroxybenzyl)benzene, 2,6-di-tert-butyl-p-cresol, and 2,2'-ethylidene-bis(4,6-di-tert-butylphenol).

In another embodiment, the second anti-oxidant additive is a benzyl compound, for example, 1,3,5-tris-(3,5-di-tert-butyl-4-hydroxybenzyl)-2,4,6-trimethylbenzene, bis-(3,5-di-tert-butyl-4-hydroxybenzyl)sulfide, isooctyl-3,5-di-tert-butyl-4-hydroxybenzyl-mercaptoacetate, bis-(4-tert-butyl-3-hydroxy-2,6-dimethylbenzyl)dithiol-terephthalate, 1,3,5-tris-(3,5-di-tert-butyl-4,10-hydroxybenzyl)isocyanurate. 1,3,5-tris-(4-tert-butyl-3-hydroxy-2,6-dimethylbenzyl)isocyanurate, dioctadecyl-3,5-di-tert-butyl-4-hydroxybenzylphosphonate, calcium salt of monoethyl-3,5-di-tertbutyl-4-hydroxybenzylphosphonate, and 1,3,5-tris-(3,5-dicyclohexyl-4-hydroxybenzyl)isocyanurate.

Acylaminophenols may be used as antioxidants, such as for example, 4-hydroxylauric acid anilide, 4-hydroxystearic acid anilide, 2,4-bis-octylmercapto-6-(3,5-tert-butyl-4-hydroxyanilino)-s-triazine, and octyl-N-(3,5-di-tert-butyl-4-hydroxyphenyl)-carbamate.

Esters of beta-(5-tert-butyl-4-hydroxy-3-methylphenyl)-propionic acid with monohydric or polyhydric alcohols, as for example, methanol, ethanol, ethylene glycol, diethyleneglycol, triethyleneglycol, tridiethyleneglycol, neopentylglycol, 1,2-propanediol, octadecanol, 1,6-hexanediol, 1,9-nonanediol, 3-thiaundecanol, 3-thiapentadecanol, pentaerythritol, tris-hydroxyethyl isocyanurate, trimethyldexanediol, trimethylolethane, trimethylolpropane, 4-hydroxylmethyl-1-phospha-2,6,7-trioxabicyclo[2.2.2]octane, dihydroxyethyl oxalic acid diamide may also be used as antioxidants. Antioxidants may also comprise amides of beta-(3,5-di-tert-butyl-4-hydroxyphenol)-propionic acid, as for example, N,N'-bis(3,5-di-tert-butyl-4-hydroxyphenylpropionyl)-hexamethylendiamnine, N,N'-bis(3,5-di-tert-butyl-4-hydroxyphenylpropionyl)trimethylenediamine, and N,N'-bis(3,5-di-tert-butyl-4-hydroxyphenylpropionyl)-hydrazine.

In one embodiment, the second stabilizer additive is selected from one of UV absorbers and light stabilizers. The ultraviolet light absorbers and light stabilizers may include 2H-benzotriazoles, benzophenones, oxanilides, alpha-cyanocinnamates, substituted benzoate esters, or nickel salts of the O-alkyl hindered phenolic benzylphosphonates. Non-limiting examples of such UV absorbers and light stabilizers include the 2-(2'-hydroxyphenyl)-benzotriazoles, such as for example, the 5'-methyl-,3 '5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl, 3'sec-butyl-5'-tert-butyl-, 4'-octoxy, 3',5'-ditert-amyl- and 3',5'-bis-(alpha.. alpha-dimethylbenzyl)-derivatives. Suitable 2-hydroxy-benzophenones such as for example, the 4-hydroxy-4-methoxy-, 4-octoxy, 4-decyloxy-, 4-dodecyloxy-, 4-benzyloxy, 4,2',4'-trihydroxy-, and 2'-hydroxy-4,4'-dimethoxy derivative may also be used as UV absorbers and light stabilizers. UV absorbers and light stabilizers may also comprise esters of substituted and unsubstituted benzoic acids, such as for example, phenylsalicilate, (4-tertbutylphenyl)salicylate, (octylphenyl)salicylate, dibenzoylresorcinol, bis-(4-tert butylbenzoyl)resorcinol, benzoylresorcinol,5-di-tert-butyl-4-hydroxybenzoic acid, 2,4-di-tert-butyl-phenyl- and 3,5-di-tert-butyl-4-hydroxybenzoate, and their -octadecyl ester,-2-methyl-4,6-di-tert-butyl-ester; and hexadecyl-3,5-di-tert-butyl-4-hydroxybenzoate.

Other UV absorbers and light stabilizers may include acrylates, as for example, alpha-cyano-beta-diphenylacrylic acid ethyl ester or isooctyl ester, alpha-carbomethoxy cinnamic acid methyl ester, alpha-cyano-beta-methyl-p-methoxycinnamic acid methyl ester, or butyl ester; alpha-carbomethoxy-p-methoxycinnamic acid methyl ester, and N-(beta-carbomethoxy-beta-cyanovinyl)-2-methyl-indoline.

The second stabilizer additive in the form of UV absorbers and light stabilizers may also comprise oxalic acid diamides, as for example, (4,4'-di-octyloxy)oxanilide, 2,2'-di-octyloxy-5',5'-ditert-butyloxanilide, 2,2'-di-dodecyloxy-5',5'di-tert-butyl-oxanilide, 2-ethoxy-2'-ethyl-oxanilide; and N,N'-bis(3-dimethylaminopropyl)-oxalamide, 2-ethoxy-5-tert-butyl-2'-ethyloxanilide, and its mixture with 2-ethoxy-2'-ethyl-5,4-di-tert-butyloxanilide, and mixtures of ortho- and para-methoxy-as well as of o- and p-ethoxy-disubstituted oxanilides.

Other examples for UV absorbers and light stabilizers may comprise nickel compounds, as for example, nickel complexes of 2,2'-thio-bis(4-(1,1,1,3tetramethylbutyl)-phenol), such as the 1:1 or 1:2 complex, optionally with additional ligands such as n-butylamine, triethanolamine, or N-cyclohexyl-diethanolamine; nickel dibutyldithiocarbamate, nickel salts of 4-hydroxy-3,5-di-tert-butylbenzylphosphonic acid monoalkyl esters, such as the methyl, ethyl, and butyl esters; nickel complexes of ketoximes, such as 2-hydroxy-4-methyl-penyl (pentyl or phenyl?) undecyl ketoxime; and nickel complexes of 1-phenyl-4-lauroyl-5-hydroxypyrazole, optionally with additional ligands.

Sterically hindered amines may be used as UV absorbers and light stabilizers as for example bis(2,2,6,6-tetramethylpiperidyl)sebacate, bis5(1,2,2,6,6-pentamethylpiperidyl)-sebacate, n-butyl-3,5-di-tert-butyl-4-hydroxybenzyl malonic acid bis(1,2,2,6,6,-pentamethylpiperidyl)ester, 4-benzoyl-2,2,6,6-tetramethylpiperidine, 4-stearyloxy-2,2-6,6-tetramethylpiperidine, 3-n-octyl-7,7,9,9-tetramethyl-1, 3,8-triaza-spiro[4.5]decane-2,4-dione, di(1,2,2,6,6-pentamethylpiperidin-4-yl) (3,5-di-tert-butyl-4-hydroxybenzyl)-butylmalonate, tris(2,2,6,6-tetramethylpiperidin-4-yl) nitrilotriacetate, 1,2-bis(2,2,6,6-tetramethyl-3-oxopiperazin-4-yl)ethane, and 2,2,4,4-tetramethyl-7-oxa-3,20-diaza-2,1-oxodispiro[5.1.11.2]heneicosane. Amine oxides of hindered amine stabilizers are also included in the present invention. Condensation products of 1-hydroxyethyl-2,2,6,6-tetramethyl-4-hydroxy-piperidine and succinic acid, N,N'-(2,2,6, 6-tetramethylpiperidyl)hexamethylendiamine and 4-tert-octylamino-2,6-dichloro-1,3,5-s-triazine, tris-(2,2,6,6-tetramethylpiperidyl)-nitrilotriacetate, tetrakis-(2,2,6,6-tetramethyl-4-piperidyl)-1,2,3,4-butane-tetra-arbonic acid, and 1,1'(1,2-ethanediyl)-bis-(3,3,5,5-tetramethylpiperazinone); 2,4-dichloro-6-tert-octylamino-s-triazine and 4,4'-hexamethylenebis(amino-2,2,6,6-tetramethylpiperidine), 4,4'-hexamethylenebis(amino-2,2,6-6-tetramethylpiperidine) and 1,2-dibromoethane, 2,4-dichloro-6-morpholino-s-triazine and 4,4'-hexamethylenebis(amino-2,2,6,6-tetramethylpiperidine), N,N'N'',N'''-tetrakis[(4,6-bis(butyl-(2,2,6, 6-tetramethylpiperidin-4-yl)-amino-s-triazin-2-yl]-1,1-diamino-4,7-diazadecane, octamethylene bis(2,2,6,6-tetramethylpiperidin-4-carboxylate), and 4,4'-ethylenebis-(2,2,6,6-tetramethylpiperazin-3-one). These amines, typically called HALS (Hindered Amines Light Stabilizers) include butane tetracarboxylic acid 2,2,6,6-tetramethyl piperidinol esters. Such amines include hydroxylamines derived from hindered amines, such as di(1-hydroxy-2,2,6, 6-tetramethylpiperidin-4-yl) sebacate, 1-hydroxy 2,2,6,6-tetramethyl-4-benzoxypiperidine; and 1-hydroxy-2,2,6,6-tetramethyl-4-(3,5-di-tert-butyl-4-hydroxy hydrocinnamoyloxy)-piperdine; and N-(1-hydroxy-2,2,6,6-tetramethyl-piperidin-4-yl)-epsilon-caprolactam. Condensation product of 1-(2-hydroxyethyl)-2,2,6,6-tetramethyl-4-hydroxypiperidine and succinic acid, N,N',N'',N'''-tetrakis[(4,6-bis(butyl-2,2,6,6-tetramethyl-piperidin-4-yl)amino)-s-triazine-2-yl]-1,10-diamino-4,7-diazadecane, as well as mixtures of amine stabilizers containing at least one of the foregoing.

In one embodiment, the UV absorbers and light stabilizers may comprise hydroxyphenyl-s-triazines, as for example 2,6-bis-(2,4-dimethylphenyl)-4-(2-hydroxy-4octyloxyphenyl)-s-triazine, 2,6-bis(2,4-dimethylphenyl)-4-(2,4-dihydroxyphenyl)-s-triazine; 5 2,4-bis(2,4-dihydroxyphenyl)-6-(4-chlorophenyl)-s-triazine; 2,4-bis(2-hydroxy-4-(2-hydroxyethoxy)phenyl)-6-(4-chlorophenyl)-s-triazine; 2,4-bis(2hydroxy-4-(2-hydroxyethoxy)phenyl)-6-phenyl-s-triazine; 2,4-bis(2-hydroxy-4-(2-hydroxyethoxy)-phenyl)-6-(2,4-dimethylphenyl)-s-triazine; 2,4-bis(2hydroxy-4-(2-hydroxyethoxy)phenyl)-6-(4-bromo-phenyl)-s-triazine; 2,4-bis(2hydroxy-4-(2-acetoryethoxy)phenyl)-6-(4-chlorophenyl)-s-triazine, and 2,4-bis(2,4-dihydroxyphenyl)-6-(2,4-dimethylphenyl)-1-s-triazine.

In yet another embodiment, metal deactivators as for example N,N'-diphenyloxalic acid diamide, N-salicylal-N'-salicyloylhydrazine, N,N'-bis-salicyloylhydrazine, N,N'-bis-(3,5-di-tert-butyl-4-hydrophenylpropionyl)-2-hydrazine, salicyloylamino-1,2,4-triazole, bis-benzyliden-oxalic acid dihydrazide, oxanilide, isophthalic acid dihydrazide, sebacic acid-bis-phenylhydrazide, bis-benzylidebeoxalic acid dihydrazide, N-salicylol-N'-salicylalhydrazine, 3-salicyloyl-amino-1,2,4-triazole or N,N-bis-salicyloyl-thiopropionic acid dihydrazide may also be used.

Peroxide scavengers, such as for example, the esters of beta-thiodipropionic acid, such as for example the lauryl, stearyl, myristyl or tridecyl esters; mercaptobenzimidazole or the zinc salt of 2-mercaptobenzimidazole, zinc-dibutyldithiocarbamate, dioctadecyldisulfide, and pentaerythritol tetrakis(.beta.-dodecylmercapto)propionate may also be used.

The second stabilizer additive may be a hydroxylamine, as for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine, N,N-di-tert-butylhydroxylamine, N-cyclohexylhydroxylamine, N-cyclododecylhydroxylamine, N,N-dicyclohexylhydroxylamine, N,N-dibenzylhydroxylamine, N,N-didecylhydroxylamine, N,N-di(coco alkyl)hydroxylamine, N,N-di($C_{20}$-$C_{22}$ alkyl) hydroxylamine, and N,N-dialkylhydroxylamine derived from hydrogenated tallow amine (that is, N,N-di (tallow alkyl)hydroxylamine); as well as mixtures containing any of the foregoing.

In one embodiment, the second stabilizer additive is a nitrone, as for example, N-benzyl-alpha-phenyl nitrone, N-ethyl-alpha-methyl nitrone, N-octyl-alpha-heptyl nitrone, N-lauryl-alpha-undecyl nitrone, N-tetradecyl-alpha-tridecyl nitrone, N-hexadecyl-alpha-pentadecyl nitrone, N-octadecyl-alpha-heptadecylnitrone, N-hexadecyl-alpha-heptadecyl nitrone, N-octadecyl-.alpha-pentadecyl nitrone, N-heptadecyl-alpha-heptadecyl nitrone, N-octadecyl-alpha-hexadecyl nitrone, and nitrone derived from N,N-dialkylhydroxylamines derived from hydrogenated tallow amines.

In yet another embodiment, the optional second stabilizer additive is a trialkyl amine oxide, as for example GENOX™ EP (commercially available from GE Specialty Chemicals) and described in U.S. Pat. Nos. 6,103,798; 5,922,794; 5,880,191; and 5,844,029.

In yet another embodiment, the optional second stabilizer additive is a polyamide stabilizer, such as for example, copper salts in combination with iodides and/or phosphorus compounds and salts of divalent manganese.

Basic co-stabilizers and neutralizers, for example, melamine, polyvinylpyrrolidone, dicyandiamide, triallyl cyanurate, urea derivatives, hydrazine derivatives, amines, polyamides, and polyurethanes; alkali metal salts and alkaline earth metal salts of higher fatty acids, such as for example, calcium stearate, calcium stearoyl lactate, calcium lactate, zinc stearate, magnesium stearate, sodium ricinoleate, and potassium palmitate; antimony pyrocatecholate, zinc pyrocatecholate, and hydrotalcites and synthetic hydrotalcites may also be used. Lithium, sodium, magnesium, calcium, and aluminum. In other embodiments, hydroxy carbonates, magnesium zinc hydroxycarbonates, magnesium aluminium hydroxycarbonates, and aluminium zinc hydroxycarbonates; as well as metal oxides, such as zinc oxide, magnesium oxide and calcium oxide may also be used.

Nucleating agents, for example, 4-tert-butylbenzoic acid, adipic acid, diphenylacetic acid, sodium salt of methylene bis-2,4-dibutylphenyl, cyclic phosphate esters, sorbitol tris-benzaldehyde acetal, and sodium salt of bis(2,4-di-t-butylphenyl) phosphate or sodium salt of ethylidene bis(2,4-di-t-butyl phenyl)phosphate may also be used in some embodiments.

In one embodiment, the optional (i.e., the second) additives and stabilizers described herein are present in an amount effective to further improve the composition stability.

The stabilizer combinations may be incorporated into the polymer resins by conventional techniques, at any convenient stage prior to the manufacture of shaped articles therefrom. In one embodiment, the second/conventional stabilizer additive is added in an amount of about 0.001 to about 5 weight percent based on the weight of the resin. In a second embodiment, about 0.0025 to about 2 weight percent. In a third embodiment, from about 0.005 to about 1 weight percent.

OTHER OPTIONAL ADDITIVES. Besides a second stabilizer additive, other components may be optionally included, e.g., fillers and reinforcing agents such as calcium carbonate, silicates, glass fibers, asbestos, talc, kaolin, mica, barium sulfate, metal oxides and hydroxides, carbon black and graphite. Furthermore, other additives may be added, for example, plasticizers, epoxidized vegetable oils, such as epoxidized soybean oils, lubricants like stearyl alcohol, emulsifiers, pigments, optical brighteners, flameproofing agents, anti-static agents, blowing agents, antiblocking agents, clarifiers, antiozonants, optical brighteners, flameproofing agents, and thiosynergists such as dilaurythiodipropionate, distearylthiodipropionate, neopentanetetrayl, tetrakis(3-dodecylthioproprionate).

PROCESSING METHODS. The stabilizers of this invention help with the stabilization of polymer resin compositions especially in high temperature processing against changes in melt index and/or color, even though the polymer resin may undergo a number of extrusions. The stabilizers of the present invention may readily be incorporated into the resin compositions by conventional techniques, at any convenient stage prior to the manufacture of shaped articles therefrom. For example, the stabilizer may be mixed with the resin in dry powder form, or a suspension or emulsion of the stabilizer may be mixed with a solution, suspension, or emulsion of the polymer.

The polymer resin compositions of the present invention can be prepared by a variety of methods, e.g., intimate admixing of the ingredients with any additional materials desired in the formulation. Suitable procedures include solution blending and melt blending. Because of the availability of melt blending equipment in commercial polymer processing facilities, melt processing procedures are generally preferred. Examples of equipment used in such melt compounding methods include: co-rotating and counter-rotating extruders, single screw extruders, disc-pack processors and various other types of extrusion equipment.

All of the ingredients may be added initially to the processing system, or else certain additives may be pre-compounded with each other or with a portion of the polymer resin to make a stabilizer concentrate. Those of ordinary skill in the art will be able to adjust blending times and temperatures, as well as component addition location and sequence, without undue additional experimentation. While the stabilizers of this invention may be conveniently incorporated by conventional techniques into polymer resins before the fabrication thereof into shaped articles, it is also possible to apply the instant stabilizers by a topical application to the finished articles.

Articles comprising the phosphite stabilizer compounds of the present invention may be made by extrusion, injection molding, blow molding, rotomolding, compaction, and other methods.

EXAMPLES

The following examples are included to provide additional guidance to those skilled in the art in practicing the claimed invention.

Synthesis of di-Tricyclodecyl-benzyl-3-heptyl phosphite: A mixture of Tricyclodecyl methanol (0.03 moles, 5.0 grams) and Triphenyl phosphite (0.015 moles, 4.65 grams) and Sodium methoxide (0.05 grams) is heated to 130° C. for two hours. The phenol is then distilled off under reduced pressure. The mixture is cooled and 2-benzyl-heptane-1-ol (0.015 moles, 3.09 grams) is added to the above mixture. The reaction is heated to 130° C. for two hours followed by removal of phenol under reduced pressure (30 millimeters of mercury) at 70–80° C. The pressure is then brought down to 2 millimeters of mercury to remove any unreacted alcohol if present. The reaction mixture is cooled to room temperature and the colorless di-tricyclodecyl benzyl-3-heptyl phosphite (8.32 grams) is stored under nitrogen. $^1$H NMR (CDCl$_3$): delta 0.84–0.99(t, 3H, CH$_3$), 1.15–2.2(m, 36H, CH$_2$), 2.3–2.8(m, 6H, CH and Benzylic CH$_2$), 3.5–3.9(m, 6H, OCH$_2$), 7.14–7.37 (m, 5H, Aromatic); $^{31}$P NMR (CDCl$_3$): δ delta 140.4 (s, trivalent phosphorous).

Synthesis of Tricyclodecyl-didecylmethyl phosphite: A mixture of tricyclodecyl methanol (0.015 moles, 2.5 grams) and triphenyl phosphite (0.015 moles, 4.65 grams) and sodium methoxide (0.05 grams) is heated to 130° C. for two hours. The phenol is then distilled off under reduced pressure. The mixture is cooled and decyl alcohol (0.03 moles, 4.74 grams) is added to the above mixture. The reaction is heated to 130° C. for two hours followed by removal of phenol under reduced pressure (30 millimeters of mercury) at 70–80° C. The pressure is then brought down to 2 millimeters of mercury to remove any unreacted alcohol if present. The reaction mixture is cooled to room temperature and the colorless Tricyclodecyl-didecylmethyl phosphite (7.52 grams) is stored under nitrogen. $^1$H NMR (CDCl$_3$): delta 0.85–0.95(t, 6H, CH$_3$), 1.2–2.4(m, 41H, CH$_2$ and CH), 3.5–3.9(m, 6H, OCH$_2$); $^{31}$P NMR (CDCl$_3$): delta 140.53 (s, trivalent phosphorous).

Synthesis of Tris(tricyclodecylmethyl) phosphite: Tricyclodecyl methanol (0.03 moles, 4.98 grams) is added to a mixture of Triphenyl phosphite (0.01 moles, 3.1 grams) and catalytic amount of Sodium methoxide (0.05 grams) under nitrogen atmosphere. The mixture is heated to 135° C. for two hours and was then distilled under reduced pressure (30 millimeters of mercury) at 70–80° C. to remove phenol completely from the reaction mixture. The pressure further is reduced by 2 millimeters of mercury to distill the excess of alcohol and trace amount of residual phenol. The reaction mixture is cooled to room temperature and the pure tris (tricyclodecylmethyl) phosphite obtained as a colorless liquid (4.2 grams) is stored under nitrogen. $^1$H NMR (CDCl$_3$): delta 1.0–2.5(m, 15H, CH$_2$ and CH), 3.5–3.7(dd, 2H, OCH$_2$); $^{31}$P NMR (CDCl$_3$): delta 140 (s, trivalent phosphorous).

Yellow Index and Melt Flow Rate Examples: In the examples, a base resin comprising 100 parts of untsabilized linear low density polyethylene (Phillips D-140 LLDPE) with 0.05 parts of zinc stearate and 0.05 parts of octadecyl 3,5-di-(tert)-butyl-4-hydroxyhydrocinnamate (Ultranox 276 obtained from GE Specialty Chemicals, Inc. of Morgantown, WV) is blended with a test stabilizer (as indicated in the tables below) using a Turbula Blender for 30 minutes.

The test stabilizer if liquid is pre-blended with the resin and mixed well using Turbula Blender. The stabilized resin formulation is extruded at 100 rotations per minute from a 1 inch (2.54 centimeter) diameter extruder at 450° F. (230° C.) in a Killion extruder. After each of the first, third and fifth extrusions, resin pellets are compression molded into 125 mil (3.2 millimeter) thick plaques at 370° F. (188° C.).

The specimen samples are measured for yellowness index (YI). Low YI values indicate less yellowing. The lower the YI value, the more effectively does the stabilizer system prevent yellowing and damage of the organic polymeric material. The melt flow rate (in grams/10 minutes) per ASTM-D-1238 (190 C./2.16 Kg, 190 C. /21.6 Kg referred to as I-2 and I-21 respectively in Table 1) is also measured on the pellets after the first, third and fifth extrusions. The closer the melt flow rate is after the fifth extrusion relative to the melt flow rate after the first extrusion, the more effective is the process stabilization achieved. The results are presented in Table 1.

In Table 1, the abbreviations used are U276 for 3,5-bis (1,1-dimethylethyl)-4-hydroxybenzenepropanoic acid octadecyl ester, Zn Stearate for zinc Stearate, TLP for trilaurylphosphite (Comparative Examples), TNPP for Tris(p-nonylphenyl)phosphite, Stabilizer A for tris (tricyclodecylmethyl) phosphite, and TIPA for Tris-isopropanolamine.

TABLE 1

| Formulation | Ex 1 | Ex 2 | Ex 1* | Ex 2* |
|---|---|---|---|---|
| Zn Stearate | 500 | 500 | 500 | 500 |
| U 276 | 500 | 500 | 500 | 500 |
| Stabilizer A | 1200 | 1500 | NA | NA |
| TLP | NA | NA | 1200 | 1500 |
| Melt Flow (I-21) Data | | | | |
| Compound | 14.464 | 14.518 | 14.372 | 14.437 |
| 1st Pass | 14.652 | 14.628 | 14.302 | 14.686 |
| 3rd Pass | 14.798 | 14.899 | 14.208 | 14.646 |
| 5th Pass | 14.564 | 14.778 | 12.922 | 13.796 |
| Melt Flow (I-2) Data | | | | |
| Compound | 0.901 | 0.896 | 0.902 | 0.903 |
| 1st Pass | 0.896 | 0.917 | 0.916 | 0.915 |
| 3rd Pass | 0.856 | 0.915 | 0.841 | 0.898 |
| 5th Pass | 0.837 | 0.910 | 0.625 | 0.751 |
| Yellowness Index (YI) | | | | |
| Compound | −4.29 | −3.63 | −3.71 | −3.75 |
| 1st pass | −3.83 | −3.23 | −3.46 | −3.48 |
| 3rd pass | −3.43 | −2.66 | −2.94 | −3.03 |
| 5th pass | −2.76 | −2.16 | −2.15 | −2.18 |

Ex 1* and Ex 2*: comparative examples
NA: not applicable
Stabilizer A: Tris(tricyclodecyl methanol)phosphite.
TLP: Tri-laurylphosphite.
Zn Stearate: Zinc Stearate.

Comparative formulations 1 and 1*; and 2 and 2* with equal loading levels between tris(tricyclodecylmethyl) phosphite and tri-laurylphosphite, as shown above indicate that tris(tricyclodecylmethyl) phosphite shows comparable melt index properties compared to tri-laurylphosphite. The closer the values of the melt flow rate after the fifth extrusion is to the value after the first extrusion is indicative of improved/desired process stabilization. Better molecular weight control in the resin measured under two different conditions are found with the tris(tricyclodecylmethyl) phosphite while the color values are comparable. The examples of the present invention show excellent (improved) hydrolytic stability and melt index properties to compared to a stabilizer additive in the prior art, namely, tri-laurylphosphite. The performance is comparable with TLP.

Hydrolytic Stability Examples. In these examples, hydrolytic stability comparison is made by exposing approximately one gram of the sample of each of the phosphites by placing each sample in a 20 milliliter scintillation vial and then kept in a humidity chamber (Thunder Scientific Model 2500) maintained at a relative humidity of about 70 percent at about 30° C. The weight gain is recorded over a period of time. A one percent weight gain is recorded over a period of time. The study ended when the sample gained a weight of about one percent. The longer the sample took to pick up the moisture, the better the hydrolytic stability.

Table 2 shows the results of the hydrolytic stability. A comparative study of the hydrolytic stability of tris(tricyclodecylmethyl)phosphite (stabilizer A in Table 2) with the stabilizers in prior art like TNPP (tris(p-nonylphenyl)phosphite) and TLP (tri-laurylphosphite) indicate that the hydrolytic stability of tris (tricyclodecylmethyl) phosphite to be quite good.

TABLE 2

Results of the hydrolytic stability

| Example Number | Compound | Hydrolytic Stability (Hours to 1% weight gain at 30 C. and at 70% relative humidity) |
|---|---|---|
| Ex 3* | TNPP | 67 |
| Ex 4* | TLP | 54 |
| Ex 3 | Stabilizer A | 506 |
| Ex 4 | Stabilizer A + 1% TIPA | 585 |

Stabilizer A: Tris(tricyclodecyl methanol)phosphite.
TLP: Tri-laurylphosphite.
TNPP: Tris(p-nonylphenyl) phosphite.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A phosphite composition of the formula:

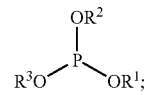

wherein $R^1$ is a substituted or an unsubstituted tricyclodecylmethyl group; and $R^2$ and $R^3$ are independently selected from the group consisting of substituted and unsubstituted tricyclodecylmethyl groups, and substituted and unsubstituted $C_6$–$C_{18}$ aliphatic, aralkyl, and alkylaryl groups.

2. The phosphite composition of claim 1, wherein $R^1$, $R^2$, and $R^3$ are 5-tricyclodecylmethyl groups.

3. The phosphite composition of claim 1, wherein $R^2$ and $R^3$ are independently selected from $C_8$–$C_{18}$ aliphatic, aralkyl, and alkylaryl groups.

4. The phosphite composition of claim 1, wherein $R^2$ and $R^3$ are independently selected from substituted and unsubstituted n-octyl, iso-octyl, tricyclodecyl, n-decyl, isodecyl, 2-benzylheptyl, dodecyl, tetradecyl, hexadecyl and octadecyl groups.

5. The phosphite composition of claim 1, wherein $R^1$ is a 5-tricyclodecylmethyl group; and $R^2$ and $R^3$ are independently selected from n-octyl, iso-octyl, tricyclodecyl, n-decyl, isodecyl, 2-benzylheptyl, dodecyl, tetradecyl, hexadecyl and octadecyl groups.

6. A phosphite composition of the formula:

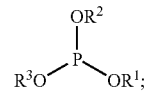

wherein $R^1$, $R^2$, and $R^3$ are 5-tricyclodecylmethyl groups.

* * * * *